United States Patent [19]

Yoshida et al.

[11] Patent Number: 5,171,836
[45] Date of Patent: Dec. 15, 1992

[54] ANTIBIOTICS PLUSBACIN

[75] Inventors: Tadashi Yoshida; Jun'ichi Shoji, both of Osaka; Teruo Hattori, Hyogo; Koichi Matsumoto, Osaka, all of Japan

[73] Assignee: Shionogi & Co., Ltd., Osaka, Japan

[21] Appl. No.: 545,565

[22] Filed: Jun. 29, 1990

[30] Foreign Application Priority Data

Jul. 24, 1989 [JP] Japan .................................. 1-192317
Aug. 24, 1989 [JP] Japan .................................. 1-218238
Oct. 6, 1989 [JP] Japan .................................. 1-262634

[51] Int. Cl.$^5$ .................. C12P 21/04; C12R 1/38; C07K 7/54
[52] U.S. Cl. .................................. 530/317; 435/71.3; 435/253.3; 530/321
[58] Field of Search ............... 530/317, 321; 435/71.3, 435/253.3, 874

[56] References Cited

U.S. PATENT DOCUMENTS

| | | | |
|---|---|---|---|
| 4,208,403 | 6/1980 | Hamill et al. | |
| 4,409,210 | 10/1983 | Kawaguchi et al. | 530/317 |
| 4,533,631 | 8/1985 | Kawaguchi et al. | 435/71.3 |
| 4,977,083 | 12/1990 | Boeck | 530/317 |
| 5,028,590 | 7/1991 | Fukuda et al. | 530/317 |
| 5,039,789 | 8/1991 | Fukuda et al. | 530/317 |

FOREIGN PATENT DOCUMENTS 0037736 10/1981 European Pat. Off. .

Primary Examiner—Herbert J. Lilling
Attorney, Agent, or Firm—Birch, Stewart, Kolasch & Birch

[57] ABSTRACT

This invention provides a novel compound of the formula:

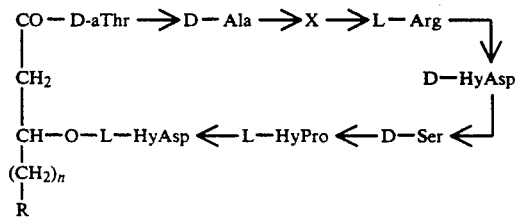

wherein X is L-HyPro or L-Pro, R is —CH$_3$ or —CH(CH$_3$)$_2$, and n is an integer from 9 to 12, or its salt, a process for producing the compound which comprises cultivating a microorganism which belongs to the genus Pseudomonas and produces the compound in a medium and recovering the compound from the medium and a biologically pure culture of Pseudomas sp. PB-6250 producing the compound.

15 Claims, 1 Drawing Sheet

ANTIBIOTICS PLUSBACIN

BACKGROUND OF THE INVENTION

1. Field of the Invention

This invention relates to a novel antibiotic Plusbacin. In particular, it relates to a compound having a antibacterial activity and produced by cultivating a microorganism which belongs to the genus Pseudomonas and produces Plusbacin.

The novel compound of the present invention is represented by the formula:

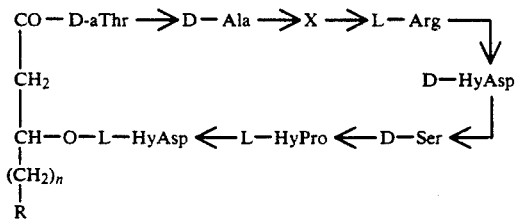

wherein X is L-HyPro or L-Pro, R is —$CH_3$ or —$CH(CH_3)_2$, and n is an integer from 9 to 12, or its salt. A compound of the above formula has been designated as "Plusbacin".

2. Prior Art

As a result of recent frequent use of antibiotics, the generation of bacteria having multiple drug resistance, especially methicillin-resistant bacteria, has become serious clinical problems. The methicillin-resistant bacteria are resistant not only to methicillin but also to many other antibiotics including aminoglycosides, tetracyclines, cephems, penicillins, carbapenems, and macrolides. Therefore, there has been a strong demand for a compound having an excellent antibacterial activity against methicillin-resistant bacteria.

As an antibiotic having lipopeptide structure like the compound of this invention, there may be exemplified Daptomycin (JP Unexamd. Pat. Publn. No. 92353/1980). However, Daptomycin is structurally different from the compound of this invention.

SUMMARY

This invention relates to a novel antibiotic Plusbacin a strong antibacterial activity against methicillin-resistant bacteria and produced by cultivating a microorganism which belongs to the genus Pseudomonas and produces Plusbacin.

The novel compound of the present invention is represented by the formula:

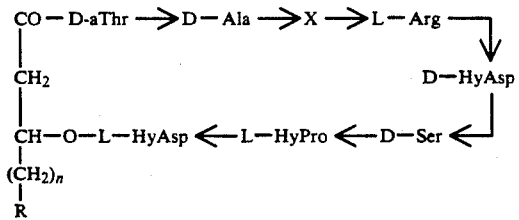

wherein X is L-HyPro or L-Pro, R is —$CH_3$ or —$CH(CH_3)_2$, and n is an integer from 9 to 12, or its salt.

At present, infections with methicillin-resistant bacteria are serious problems in a clinical field and there has been sought a compound having an excellent antibacterial activity against these bacteria. Since the compound of this invention has a strong antibacterial activity against methicillin-resistant bacteria, especially Staphylococcus aureus, it can greatly contribute to a replenishment of medicine.

DETAILED DESCRIPTION OF THE INVENTION

Figure 1A:
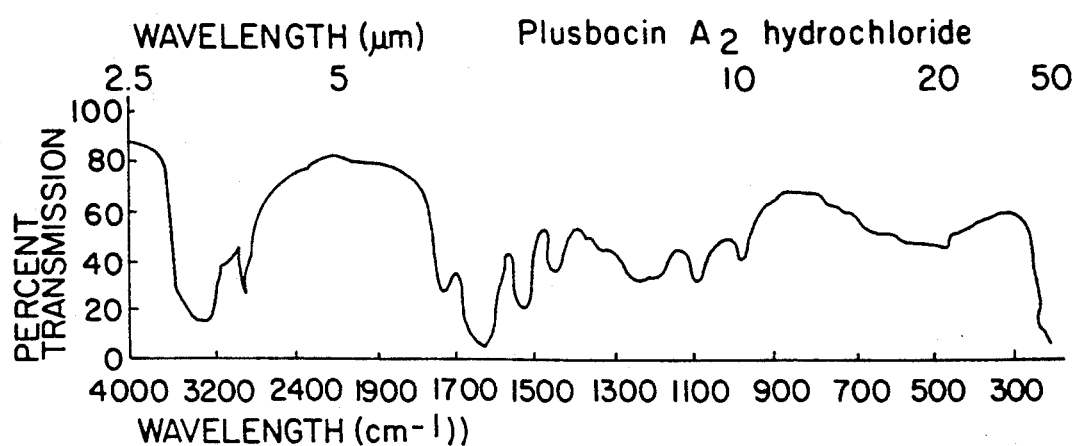
FIG. 1 shows IR spectra of Plusbacin $A_2$ and $B_2$ hydrochlorides.

The inventors found that a strain belonging to the genus Pseudomonas produces a compound represented by the formula:

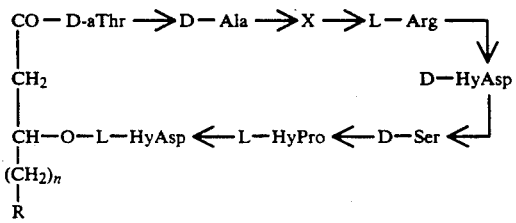

wherein X is L-HyPro or L-Pro, R is —$CH_3$ or $CH(CH_3)_2$, and n is an integer from 9 to 12 having a strong antibacterial activity against methicillin-resistant bacteria.

The methicillin-resistant Staphylococcus aureus has cross resistance to many antibiotics. Therefore, it is very important to provide an antibiotic unfailingly effective against methicillin-resistant Staphylococcus aureus. The compound of this invention shows a strong antibacterial activity against methicillin-resistant S. aureus and is therefore highly useful.

In the above-mentioned compounds, when X is L-HyPro, n is 10, and R is —$CH_3$, the compound is called Plusbacin $A_1$; when X is L-HyPro, n is 9, and R is —$CH(CH_3)_2$, the product is called Plusbacin $A_2$; when X is L-HyPro, n is 10, and R is —$CH(CH_3)_2$, it is called Plusbacin $A_3$; when X is L-HyPro, n is 12, and R is —$CH_3$, it is called Plusbacin $A_4$; and in case X is L-Pro, n is 10, and R is —$CH_3$, the product is called Plusbacin $B_1$; and when X is L-Pro, n is 9, and R is —$CH(CH_3)_2$, it is called Plusbacin $B_2$; and when X is L-Pro, n is 10, and R is —$CH(CH_3)_2$, the compound is called Plusbacn $B_3$; and when X is L-Pro, n is 12, and R is —$CH_3$, it is called Plusbacin $B_4$. This invention provides not only these compounds but also their salts.

As for salts, there are exemplified salts formed with such materials as alkali metals such as lithium, potassium and sodium; alkali earth metals such as magnesium and calcium; inorganic acids such as hydrochloric acid, sulfuric acid, nitric acid, phosphoric acid and hydrobromic acid; and organic acids such as acetic acid, oxalic acid, maleic acid, fumaric acid, citric acid, malic acid, adipic acid, and succinic acid.

In this invention, Plusbacin means any one of the above-mentioned 8 compounds, but it also means all these compounds depending on circumstances.

Abbreviations used herein have the following meanings:

L-HyPro: L-trans-3-hydroxyproline
D-HyAsp: D-threo-β-hydroxyaspartic acid
L-HyAsp: L-threo-β-hydroxyaspartic acid aThr: allo-threonine The physicochemical properties of the compounds of this invention are mentioned below:

Physicochemical Properties

Properties: Plusbacin $A_1$–$A_4$ and $B_1$–$B_4$ are extremely similar to one another in properties. They are amphoteric and their hydrochlorides are obtained as colorless powder.

Solubility: Each of the hydrochlorides is readily soluble in methanol and dimethyl sulfoxide, slightly soluble in ethanol, insoluble in acetone, ethyl acetate and chloroform. The hydrochlorides are very slightly soluble in purified water, but are soluble in alkaline water.

HPLC: None of the components of Plusbacin can be separated by TLC (thin-layer chromatography), but each component can be separated by HPLC (high-performance liquid chromatography). The conditions of HPLC are shown below, and eluted volumes are shown in Table 1.

HPLC Conditions

Chromatogram 1

Column: Ultron 7CN 4.6×250 mm
Mobile phase: 50 mM phosphate buffer solution, pH 2.2, containing acetonitrile-50 mM sodium sulfate (25:75)
Flow rate: 1.575 ml/min
Detection: UV 220 nm

Chromatogram 2

Column: Nucleosil 5$C_{18}$ 4.6×150 mm
Mobile phase: 50 mM phosphate buffer solution, pH 7.5, containing acetonitrile-50 mM sodium sulfate (34:66)
Flow rate: 1.575 ml/min
Detection: UV 220 nm

TABLE 1

Analysis of Plusbacin $A_1$–$A_4$ and $B_1$–$B_4$, by HPLC

| | \multicolumn{8}{c}{Eluted volume (ml)} | | | | | | | |
|---|---|---|---|---|---|---|---|---|
| | $A_1$ | $B_1$ | $A_2$ | $B_2$ | $A_3$ | $B_3$ | $A_4$ | $B_4$ |
| Chromatogram 1 | 14.5 | 16.4 | 18.9 | 21.4 | 26.5 | 30.5 | 28.2 | 32.3 |
| Chromatogram 2 | 6.0 | 6.5 | 9.0 | 9.6 | 15.6 | 16.4 | 17.2 | 18.7 |

Color reaction

Ninhydrin reaction: Negative
Sakaguchi's reaction: Positive

Elementary analysis

As for molecular formula of Plusbacin $A_2$, it was determined to be $C_{49}H_{81}N_{11}O_{20}$ based on the results of the elementary analysis of its sodium salt and the analysis of its hydrochloride with a high resolution mass spectrometer.

Anal Calcd. (%) for $C_{49}H_{80}O_{20}Na \cdot H_2O$: C 49.70, H 6.98, N 13.01, Na 1.94; Found (%): C 49.54, H 7.09, N 12.76, Na 1.91.

Mass spectrometry: m/z 1144.5735 ($MH^+$)

As for the compounds other than Plusbacin $A_2$, they were determined to be as follows, based on the results of the analysis with a high resolution mass spectrometer:

Plusbacin $A_1$

Molecular formula: $C_{48}H_{79}N_{11}O_{20}$
Mass spectrometry: m/z 1130.5569 ($MH^+$)

Plusbacin $B_1$

Molecular formula: $C_{48}H_{79}N_{11}O_{19}$
Mass spectrometry: m/z 1114.5614 ($MH^+$)

Plusbacin $B_2$

Molecular formula: $C_{49}H_{81}N_{11}O_{19}$
Mass spectrometry: m/z 1128.5796 ($MH^+$)

Plusbacin $A_3$

Molecular formula: $C_{50}H_{83}N_{11}O_{20}$
Mass spectrometry: m/z 1158.5883 ($MH^+$)

Plusbacin $B_3$

Molecular formula: $C_{50}H_{83}N_{11}O_{19}$
Mass spectrometry: m/z 1142.5943 ($MH^+$)

Plusbacin $A_4$

Molecular formula: $C_{50}H_{83}N_{11}O_{20}$
Mass spectrometry: m/z 1158.5893 ($MH^+$)

Plusbacin $B_4$

Molecular formula: $C_{50}H_{83}N_{11}O_{19}$
Mass spectrometry: m/z 1142.5934 ($MH^+$)

No elementary analysis was performed on any of the compounds other than Plusbacin $A_2$. As the molecular formulas have been determined with a high resolution mass spectrometer, it was not necessary to perform elementary analysis.

Amino Acids and Fatty Acids Constituting the Compound

Each compound was hydrolyzed at 110° C. for 20 hours with constant boiling point hydrochloric acid, and then subjected to analysis with an amino acid automatic analyzer. As a result, amino acids shown in Table 2 were detected. Fatty acids were extracted with ether from hydrolyzate obtained after hydrolysis at 110° C. for 4 hours with constant boiling point hydrochloric acid. The substances obtained were turned into methyl esters with trimethylsilyldiazomethane, and then subjected to analysis by gas chromatography, followed by comparison with reference materials and mass spectrometry. As a result, fatty acids shown in Table 2 were found.

TABLE 2

Amino acids and fatty acids constituting Plusbacin $A_1$–$A_4$ and $B_1$–$B_4$

| | HyAsp | HyPro | Thr | Ser | Pro | Ala | Arg | Fatty acids |
|---|---|---|---|---|---|---|---|---|
| | | | (μm/mg) | | | | | |
| $A_1$ | 1.50 | 1.34 | 0.69 | 0.66 | 0.00 | 0.75 | 0.75 | n-$C_{14}h^3$ |
| | (2) | (2) | (1) | (1) | | (1) | (1) | |
| $A_2$ | 1.58 | 1.55 | 0.71 | 0.71 | 0.00 | 0.77 | 0.77 | i-$C_{15}h^3$ |
| | (2) | (2) | (1) | (1) | | (1) | (1) | |
| $A_3$ | 1.54 | 1.55 | 0.70 | 0.71 | 0.00 | 0.77 | 0.77 | i-$C_{16}h^3$ |
| | (2) | (2) | (1) | (1) | | (1) | (1) | |
| $A_4$ | 1.45 | 1.38 | 0.66 | 0.64 | 0.00 | 0.71 | 0.71 | n-$C_{16}h^3$ |
| | (2) | (2) | (1) | (1) | | (1) | (1) | |
| $B_1$ | 1.69 | 0.76 | 0.79 | 0.76 | 0.83 | 0.87 | 0.86 | n-$C_{14}h^3$ |
| | (2) | (1) | (1) | (1) | (1) | (1) | (1) | |
| $B_2$ | 1.54 | 0.71 | 0.70 | 0.69 | 0.74 | 0.77 | 0.75 | n-$C_{15}h^3$ |
| | (2) | (1) | (1) | (1) | (1) | (1) | (1) | |
| $B_3$ | 1.47 | 0.62 | 0.67 | 0.65 | 0.71 | 0.75 | 0.72 | n-$C_{16}h^3$ |
| | (2) | (1) | (1) | (1) | (1) | (1) | (1) | |

TABLE 2-continued

| | Amino acids and fatty acids constituting Plusbacin $A_1$-$A_4$ and $B_1$-$B_4$ | | | | | | | |
|---|---|---|---|---|---|---|---|---|
| | HyAsp | HyPro | Thr | Ser | Pro | Ala | Arg | |
| | | | | (μm/mg) | | | | Fatty acids |
| $B_4$ | 1.49 (2) | 0.67 (1) | 0.68 (1) | 0.66 (1) | 0.70 (1) | 0.76 (1) | 0.74 (1) | n-$C_{16}h^3$ |

Figure 1B:
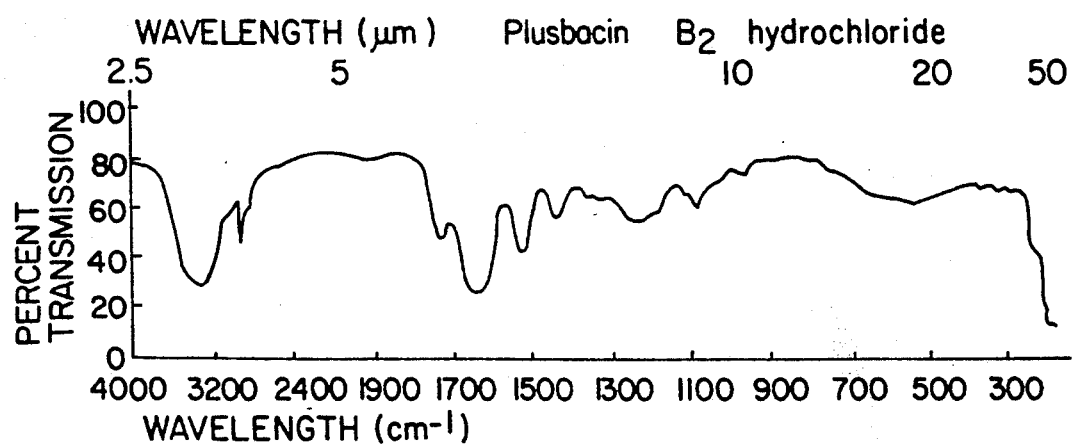

( ): Molar ratio
HyAsp: β-hydroxy aspartic acid
HyPro: L-trans-3-hydroxyproline
n-$C_{14}h^3$: 3-hydroxy tetradecanoic acid
i-$C_{15}h^3$: 3-hydroxy isopentadecanoic acid
n-$C_{16}h^3$: 3-hydroxy hexadecanoic acid
i-$C_{16}h^3$: 3-hydroxy isohexadecanoic acid UV spectrum: Terminal absorption IR spectrum: In IR spectrum, each of the compounds showed absorption similar to one another. As representative absorptions, IR spectra of Plusbacin $A_2$ hydrochloride and $B_2$ hydrochloride are shown in FIG. 1.

From the physicochemical properties and various chemical analysis mentioned above, Plusbacin, the compound of this invention, is deduced to have the following formula:

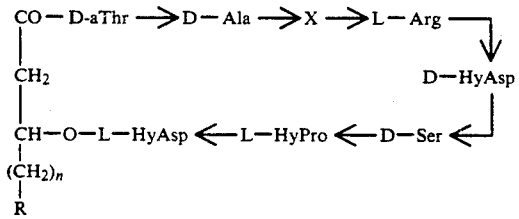

wherein X is L-HyPro or L-Pro, R is —$CH_3$ or —$CH(CH_3)_2$, and n is an integer from 9 to 12.

As shown above, Plusbacin is an acylpeptide with a new structure.

The strain producing Plusbacin of this invention has the following bacteriological properties:

(1) MORPHOLOGICAL PROPERTIES

Cells of the microorganism grown on heart infusion agar (Difco) for 24 hours at 28° C. were examined with a scanning electron microscope showed the following characteristics: Cells are slightly slender rods, their sizes are 2-3 (μm)×0.5-0.7 (μm). They look like Vienna sausage in shape, with rounded ends. Most of them do not have flagella, but a few of them have one or more slender, and delicate polar ones. Therefore, these grown in liquid media showed a slight motility as mentioned later.

(2) GRAM-STAINING

This microorganism is gram-negative. Gram-staining was performed on the young cells cultured on a nutrient agar slant medium for 24 hours at 28° C. Sporulation capability was not observed.

(3) CULTURAL CHARACTERISTICS

① Nutrient broth culture: The growth was scanty. Uniform turvidity was observed. No formation of pellicle was observed. No generation of gas was observed. No formation of soluble pigment was observed. Very weak motility of cells was observed.

② Nutrient agar stab culture: Very slight filiform growth was observed along the line of the stabbing. No generation of gas was observed. No formation of soluble pigment was observed. The microorganism was aerobic. The surface had a brownish gray-milky color with a dull shine.

③ Nutrient agar slant culture: The growth was abundant, and showed filiform. Colonies of the microorganism had an entire margin, but sometimes showed undulate one. As for forms of elevations, they showed raised to convex ones. No generation of gas was observed. The formation of a soluble brown pigment issued into the agar was observed. The bacterial colonies were moist and turbid, with a shining brownish cream color.

④ Nutrient agar plate culture: Colonies were round and turbid, with an entire margin. The elevation was convex. No generation of gas was observed, but a soluble brown pigment issued into the agar was formed. They were moist, with a shining brownish cream color.

⑤ Litmus milk: Acid production was observed. The peptonization of milk was strong. A grayish red-purple, and slightly thick pellicle was formed on the surface, and a gray ring was observed on the surface parietis. The upper layer was red-purple and translucent, and the lower (one) was red-orange and translucent. Small quantities of orange-yellow precipitate were observed. No generation of gas was observed.

⑥ MacConkey agar plate: Good growth was observed. A dark brown, soluble pigment was issued into the medium.

⑦ Growth on Trypton-Soyton agar plate containing 0.2% (w/v) cetrimide: No growth was observed. The growth was inhibited by cetrimide (cetyltrimethyl ammonium bromide).

⑧ Growth on Trypton-Soyton agar plate containing 6.5% (w/v) sodium chloride: No growth was observed. The growth was inhibited by the 6.5% (w/v) sodium chloride.

⑨ Growth on Trypton-Soyton agar plate containing 1% (w/v) TTC: No growth was observed. The growth was inhibited by TTC (Triphenyltetrazolium chloride).

(4) PHYSIOLOGICAL AND BIOCHEMICAL PROPERTIES

1. Accumulation of PHB in the cell: No accumulation of PHB (Poly-β-hydroxybutyrate) was observed.
2. Catalase test: Weakly positive
3. Oxidase test: Strongly positive
4. O-F test: Oxidative (O type). Glucose was assimilated oxidatively.
5. Deoxyribonuclease test: Negative
6. Urease test: Negative
7. Ornithine decarboxylase test: Negative
8. Lysine decarboxylase test: Negative
9. Arginine dihydrolase test: Negative
10. Acylamidase test: Negative
11. Hydrolysis of gelatin: Positive. Test was performed by nutrient gelatin stab culture at room temperature (22° C.-25° C.)
12. Hydrolysis of starch: Negative
13. Lipase test (hydrolysis of Tween 80): Positive
14. Utilization of citric acid: Positive (tested by Simon's medium)
15. Reduction of nitrate to nitrite: Negative
16. Denintrification reaction: Negative
17. Formation of $H_2S$: Negative
18. Formation of indole: Negative
19. Formation of fluorescent pigment: Negative
20. VP test: Negative
21. MR test: Negative 22. Hydrolysis of esculin: Positive
23. ONPG test: Negative ($\beta$-galactosidase was not formed)
24. Phenylalanine deamination test: Negative
25. Acid formation without gas was observed on D-glucose, D-fructose, maltose and trehalose. Neither acid nor gas was formed from L-arabinose, lactose, D-mannitol, sucrose or D-xylose.
26. G+C mole % of DNA: 69.4

From the characteristics mentioned above, the Plusbacin-producing microorganism is considered to be a strain of the following description. The Plusbacin-producing microorganism is a gram-negative aerobic bacterium. It was isolated from a soil sample collected in Okinawa Prefecture. This microorganism is catalase-positive, and has no sporulating capability. Since it is oxidase-positive, it can be assigned to Pseudomonadaceae or Flavobacterium. However, according to Bergey's Manual of systematic Bacteriology, 1 (1984), the G+C mole % of DNA is 31%–42% (Tm method) in Flavobacterium. As that of the above-mentioned microorganism is 69.4% (HPLC method), an extraordinarily high value, it is not reasonable to assign it to Flavobacterium. Besides, this microorganism showed a slight motility, and flagella were found, though in a very small number of the cells of the microorganism. Therefore, it is reasonable to assign it to Pseudomonadaceae.

Now, in Pseudomonadaceae, the genus to which this microorganism is considered to be assigned is Pseudomonas or Xanthomonas. According to Bergey's Manual of Systematic Bacteriology, 1 (1984), Xanthomonas moves with a polar flagellum, and shows negative to weakly positive oxidase test. Furthermore, Xanthomonas is a short rod, its size being 0.7–1.8 ($\mu$m)×0.4–0.7 ($\mu$m). In this respect, it is different from this microorganism. The G+C mole % of DNA in Xanthomonas is 63%–71% (Tm, Bd method), and that of this microorganism is 69.4%. Therefore, in respect of the G+C mole % of DNA in Xanthomonas is is close to Xanthomonas. However, judging from the size of this microorganism, the strong positive reaction of oxidase test, and its motility, it is not reasonable to be assigned it to Xanthomonas. Therefore, the organism should be assigned to Pseudomonas. In genus Pseudomonas, none of the species registered on the Bergey's Manual of Systematic Bacteriology, 1 (1984) is identical with this microorganism. If a species close to this microorganism has to be cited, it would be *Pseudomonas paucimobilis*, but it is evidently different from this microorganism in various biochemical properties.

Meanwhile, the G+C mole % of DNA in *Pseudomonas paucimobilis* is said to be 58%–70% (Bd method). Since that of this microorganism is high with 69.4%, it is considered reasonable to assign this microorganism on Pseudomonas.

Although this microorganism may be a new species of Pseudomonas, we decided to refer it as Pseudomonas sp. PB-6250. This strain was deposited in Fermentation Research Institute, 1-3, Higashi 1-chome, Tsukuba-Shi, Ibaragi Prefecture, Japan, on Jun. 27, 1989 under the name of Pseudomonas sp. PB-6250 (FERM P-10794) and it is transfered to a new deposit under the Budapest Treaty on May 31, 1990 (FERM BP-2938).

In this invention, all strains including not only the above-mentioned Pseudomonas sp. PB-6250 and its natural and artificial variant but also all strains belonging to Pseudomonas and capable of producing at least one of the compounds Plusbacin $A_1$–$A_4$ and $B_1$–$B_4$ may be used, and therefore all such strains come under the scope of this invention.

Plusbacin is produced by first cultivating a Plusbacin-producing strain in a nutrient medium under aerobic conditions and then by separating Plusbacin from the culture after completion of cultivation.

A general process for producing Plusbacin is shown below:

As for composition of the medium and cultivating conditions, those employed generally for the production of antibiotics may be used. As a rule, the medium contains carbon and nitrogen sources, inorganic salts, etc. When necessary, vitamins and precursors may be added. As carbon source, there may be used such materials as glucose, starch, dextrin, glycerol, molasses, and organic acid, either alone or as mixture thereof. As nitrogen source, there may be used such materials as soybean powder, corn steep liquor, meat extract, yeast extract, cotton seed powder, peptone, wheat embryo, ammonium sulfate, and ammonium nitrate, either alone or as mixture thereof. As inorganic salt, there are exemplified calcium carbonate, sodium chloride, potassium chloride, magnesium sulfate, copper sulfate, manganese chloride, zinc sulfate, cobalt chloride and various phosphates, which are added to the medium if necessary.

Cultivation may be performed by a method generally employed for the production of antibiotics. Liquid culture is preferable, and for production on a large scale, deep aerobic culture is recommendable. When the pH of the medium is changeable, a buffer such as calcium carbonate may be added to the medium. The cultivation may be performed at about 20° C.–40° C., preferably at 25° C.–32° C. The cultivation time varies, greatly depending on the scale of fermentation. A period of about 1 day–7 days is usual cultivation time required for production on a large scale. When a violent foaming is happened in the course of fermentation, it is recommended to add a defoaming agent such as vegetable oil, lard or polypropylene glycol before or in the course of cultivation.

For the separation of Plusbacin from the culture after completion of cultivation, there may be used a separating method generally employed for separation from fermented products. For example, there may be used, depending on the situation, a combination of such procedures as filtration, centrifugation, adsorption or desorption with the use of various ion-exchange resins and other active adsorbents, chromatography, and/or extraction with various organic solvents.

For convenience in separation and also in use as a pharmaceutical and as an animal drug, it is preferable in some cases to make the compound into a salt. As material that can make a salt with Plusbacin, there are alkali metals such as lithium, potassium and sodium, alkaline earth metals such as magnesium and calcium, inorganic acids such as hydrochloric acid, sulfuric acid, nitric acid, phosphoric acid and hydrobromic acid, and organic acids such as acetic acid, oxalic acid, maleic acid, fumaric acid, citric acid, malic acid, adipic acid and succinic acid.

Plusbacin and its salt can be administered orally or parenterally to humans and animals as an active ingredient in an antibacterial preparation. With addition of generally used excipient, stabilizer, preservative, moistening agent, surfactant, etc., they can be made into tablets, capsules and/or powder preparations for oral administration. They can also be made into injectable preparations, liniments and/or suppositories for parenteral or external administration. Dosage level varies with therapeutic purpose, age and conditions of the patient, etc. However, in case of intravenous injection for adults, the daily dosage is about 0.01–10 g.

The following Example will further illustrate the invention, but is not limited the invention in any way.

EXAMPLE 1

(a) Production Process by Fermentation

Slant culture is suspended in a 2 l Erlenmeyer flask containing 1 l of medium consisting of 10 g of glucose, 5 g of yeast extract and 1000 ml of water (without pH adjustment) are suspended under aseptic conditions, the cells of Pseudomonas sp. PB-6250 (FERM BP-2938) grown on a cultivated slant. The suspension is cultivated with shaking at 250 rpm for 18 hours at 28° C. Seven liters of the culture is inoculated into 200 l of a medium consisting of 10 g of corn starch, 10 g of potato starch, 20 g of CA-1 (an animal feed) and 1000 ml of water (without pH adjustment), which is contained in a 500 l tank. The mixture is cultivated for 72 hours at 28° C. at 250 rpm under aeration at 200 l/minute.

(b) Extraction and Purification Processes (1) To about 200 l of the cultivated solution obtained as above is added 25 kg of sodium chloride, and its pH is adjusted to 3.0 with dilute hydrochloric acid. The mixture is centrifuged with sharples centrifuge. The portion containing wet cells is twice extracted with 54 l of 70% acetone. The extracted solution is concentrated under reduced pressure, and most of the acetone is evaporated. To the remaining aqueous solution (15 l) is added 10 l of water. The pH of the solution is adjusted to 8.0 with dilute sodium hydroxide solution. The solution is then passed through a column (10 l) containing Diaion HP-20 (Mitsubishi Chemical Industries Ltd.) so as to cause the antibiotic to be adsorbed to the adsorbent. After washing the column with water, the antibiotic is eluted by concentration gradient elution method with acetone of 30% to 100% concentration. Fractions of active eluates are collected (10 l), from which most of the acetone is evaporated under reduced pressure. The solution is then extracted with 5 l of n-butanol at pH 2.5 (adjusted with dilute hydrochloric acid). The solution extracted with n-butanol is concentrated under reduced pressure, and acetone is added to the concentrate, whereby 23.9 g of crude powder containing the antibiotic is obtained.

(2) The above-mentioned crude powder (23 g) dissolved in a mixture of chloroform, ethanol and 10% acetic acid (4:7:2) is subjected to a silica gel column (made by Merck, 70–230 mesh, 1000 g) filled with the mixture in order to develop and elute the antibiotic. Portions of active eluate are collected, which are then concentrated, while adding water and butanol. The antibiotic is extracted from the concentrate with butanol at pH 2.0. The extracted solution is washed with water, concentrated under reduced pressure and mixed with acetone, whereby 6.34 g of antibiotic is obtained as crude powder.

(3) The above crude powder is subjected to high performance liquid chromatography under the following conditions, whereby a refined fraction is obtained.

Column: YMC AP-324 S15/30 300A ODS (made by Yamamura Chemical Co.).

Mobile phase: 50 mM phosphate buffer, pH 7.5, containing acetonitrile-50 mM sodium sulfate (36:64).

Flow rate: 100 ml/minute

Detection is made at 220 nm with an UV detector. The sample is dissolved in water of pH 8.0. 500 mg is injected at a time.

With chromatography as above, a fraction containing $A_1$ and $B_1$ comes out first, followed by a fraction containing $A_2$ and $B_2$ and then a fraction containing $A_3$, $A_4$, $B_3$ and $B_4$ comes out at last. Each fraction is collected and concentrated under reduced pressure. The concentrate is extracted with butanol at pH 2.5. The extracted solution is washed with 0.1N hydrochloric acid and with water and further concentrated under reduced pressure. Acetone is added to the mixture, whereby 150 mg of a mixture of $A_1$ and $B_1$ hydrochlorides, 214 mg of a mixture of $A_2$ and $B_2$ hydrochlorides, and 1.0 g of a mixture of $A_3$, $A_4$, $B_3$ and $B_4$ hydrochlorides are obtained.

(4) Each of the compounds $A_1$–$A_4$ and $B_1$–$B_4$ is separated from the above mixtures by subjecting each mixture to high performance liquid chromatography under the following conditions:

Column: Ultron 7CN 20×250 mm (made by Shinwa Kako Co.)

Mobile phase: 50 mM phosphate buffer, pH 2.2, containing acetonitrile-50 mM sodium sulfate (26:74 for separation of $A_1$ and $B_1$, and 28:72 for separation of $B_2$, $A_3$, $B_3$, $A_4$, and $B_4$)

Flow rate: 11.25 ml/minute

Detection is made at 220 nm with an UV detector. The sample is dissolved in 50% methanol, and 5 mg is injected at a time.

The fraction of each compound is collected and concentrated under reduced pressure, followed by extraction with n-butanol at pH 2.5. The extracted solution is washed with 0.1N hydrochloric acid and with water and further concentrated under reduced pressure. Acetone is added to the concentrate, whereby a hydrocloride of each compound is obtained.

From 77 mg of a mixture of $A_1$ and $B_1$, there were obtained 23 mg of $A_1$ hydrochloride and 6 mg of $B_1$ hydrochloride.

From 100 mg of a mixture of $A_2$ and $B_2$, there were obtained 68 mg of $A_2$ hydrochloride and 4 mg of $B_2$ hydrochloride.

From 150 mg of a mixture of $A_3$, $A_4$, $B_3$ and $B_4$, there were obtained 52 mg of $A_3$ hydrochloride, 10 mg of $A_4$ hydrochloride, 5 mg of $B_3$ hydrochloride, and 2 mg of $B_4$ hydrochloride.

EFFECT OF THE INVENTION

As for the antibacterial activities of Plusbacin $A_1$–$A_4$ and $B_1$–$B_4$, in vitro tests of antibacterial activities were performed according to the test method set by the Japan Society of Chemotherapy under the following conditions:

① Preparation of a Microorganism Suspension

One platinum loop portion ($10^5$ CFU/ml) of a testing strain on the slant medium is inoculated into 1 ml of cultivating medium (agar medium for sensitivity disc, made by Nissui Co., Ltd.), which is then cultivated for 18–20 hours at 37° C. A 100-fold dilution of the cultivated product is used as a suspension of the inoculating microorganism.

② Sample Solution

9–10 mg of the sample is weighed accurately, which is then dissolved in distilled water at a concentration of ˙2 mg/ml.

③ Agar Plate

The sample solution is diluted with sterilized water by stepwise multiple dilution method (2000–0.25 μg/ml). 0.5 ml of each of the diluted sample solution is transferred to a sterilized plastic Petri dish (diameter 9 cm). To the dish is added 9.5 ml of agar medium (medium for sensitivity test, made by Eiken Chemical Co., Ltd.). The mixture is stirred slowly, after which it is allowed to solidify.

④ One platinum loop portion (0.5–1 μl) of the suspension for measurement of MIC value is transferred to each of the agar plates containing samples of different concentrations prepared as above. The mixture is cultivated for 18–20 hours at 37° C., after which the growth on the surface of the agar is observed. The lowest concentration at which the growth has been completely inhibited is taken as MIC, which is shown in terms of μg/ml.

The results are shown in Table 3.

TABLE 3

| | MIC (μg/ml) | | | | | | | |
|---|---|---|---|---|---|---|---|---|
| Testing microorganisms | Plus-bacin $A_1$ | Plus-bacin $A_2$ | Plus-bacin $A_3$ | Plus-bacin $A_4$ | Plus-bacin $B_1$ | Plus-bacin $B_2$ | Plus-bacin $B_3$ | Plus-bacin $B_4$ |
| *Staphylococcus aureus* SR5577** | 1.6 | 0.8 | 0.8 | 0.4 | 1.6 | 0.8 | 1.6 | 1.6 |
| *Staphylococcus aureus* JC-1** | 0.05 | 0.1 | 0.1 | 0.1 | 0.1 | 0.1 | 0.4 | 0.8 |
| *Staphylococcus aureus* SMITH** | 1.6 | 0.8 | 0.4 | 0.4 | 1.6 | 0.8 | 1.6 | 1.6 |
| *Staphylococcus aureus* SR5597* | 1.6 | 0.8 | 0.4 | 0.4 | 1.6 | 0.8 | 1.6 | 1.6 |
| *Staphylococcus aureus* SR5580* | 1.6 | 0.8 | 0.8 | 0.4 | 1.6 | 0.8 | 1.6 | 1.6 |
| *Staphylococcus epidermidis* A14990 | 0.8 | 0.2 | 0.2 | 0.4 | 0.8 | 0.4 | 0.8 | 1.6 |
| *Enterococcus faecalis* SR1004 | 6.3 | 0.6 | 0.8 | 0.8 | 6.3 | 1.6 | 3.1 | 6.3 |

*Methicillin-resistant microorganism.
**Methicillin-sensitive

What we claim is:

1. A compound of the formula:

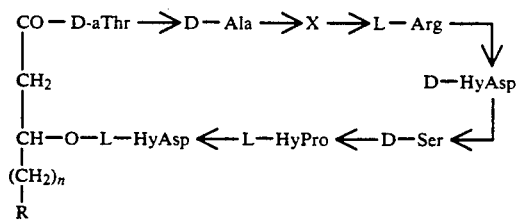

wherein X is L-HyPro or L-Pro, R is —CH$_3$ or —CH(CH$_3$)$_2$, and n is an integer from 9 to 12, or its salt.

2. A compound claimed in claim 1, wherein n is an integer of 9, 10 or 12.

3. A compound as claimed in claim 1, wherein X is L-HyPro.

4. A compound as claimed in claim 1, wherein X is L-Pro.

5. A compound as claimed in claim 1, wherein X is L-HyPro, n is 10 and R is —CH$_3$.

6. A compound as claimed in claim 1, wherein X is L-HyPro, n is 9 and R is —CH(CH$_3$)$_2$.

7. A compound as claimed in claim 1, wherein X is L-HyPro, n is 10 and R is —CH(CH$_3$)$_2$.

8. A compound as claimed in claim 1, wherein X is L-HyPro, n is 12 and R is —CH$_3$.

9. A compound as claimed in claim 1, wherein X is L-Pro, n is 10 and R is —CH$_3$.

10. A compound as claimed in claim 1, wherein X is L-Pro, n is 9 and R is —CH(CH$_3$)$_2$.

11. A compound as claimed in claim 1, wherein X is L-Pro, n is 10 and R is —CH(CH$_3$)$_2$.

12. A compound as claimed in claim 1, wherein X is L-Pro, n is 12 and R is —CH$_3$.

13. A compound as claimed in claim 1, wherein said salt is selected from the group consisting of an alkali metal salt, an alkaline earth metal salt, an inorganic acid salt and an organic acid salt.

14. A compound as claimed in claim 1, 2, 3, 4, 5, 6, 7, 8, 9, 10, 11 or 12 in a purified form.

15. A compound as claimed in claim 1, in the form of a concentrated solution.

* * * * *